· US008728012B2

(12) United States Patent
Braido

(10) Patent No.: US 8,728,012 B2
(45) Date of Patent: May 20, 2014

(54) APPARATUS AND METHOD FOR MEASURING BLOOD VESSELS

(75) Inventor: Peter N. Braido, Maple Grove, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 819 days.

(21) Appl. No.: 12/340,382

(22) Filed: Dec. 19, 2008

(65) Prior Publication Data

US 2010/0160832 A1  Jun. 24, 2010

(51) Int. Cl.
*A61B 5/117* (2006.01)
*A61B 5/103* (2006.01)
*A61B 1/00* (2006.01)
*G01B 3/10* (2006.01)

(52) U.S. Cl.
USPC ............... 600/587; 33/512; 33/555.4; 33/759

(58) Field of Classification Search
USPC ........... 600/587, 593, 481, 37, 104, 117, 585; 33/514.2, 3 A, 3 R, 511, 512, 555.4, 33/561.2, 759; 606/1, 102; 604/164.13
See application file for complete search history.

(56) References Cited

U.S. PATENT DOCUMENTS

| | | | |
|---|---|---|---|
| 2,636,281 A * | 4/1953 | Unger | 33/514.2 |
| 3,993,045 A * | 11/1976 | Ion | 600/481 |
| 4,397,617 A | 8/1983 | Sergio et al. | |
| 4,769,031 A | 9/1988 | McGough et al. | |
| 4,790,844 A | 12/1988 | Ovil | |
| 4,816,029 A | 3/1989 | Penny, III et al. | |
| 4,872,874 A | 10/1989 | Taheri | |
| 5,184,407 A * | 2/1993 | Watrous | 33/555.4 |
| 5,330,528 A | 7/1994 | Lazim | |
| 5,332,403 A | 7/1994 | Kolff | |
| 5,466,216 A | 11/1995 | Brown et al. | |
| 5,511,958 A | 4/1996 | Chen et al. | |

(Continued)

FOREIGN PATENT DOCUMENTS

WO  0035355 A2  6/2000

OTHER PUBLICATIONS

Aeba, R., et al., "Apico-Pulmonary Artery Conduit Repair of Congenitally Corrected Transposition of the Great Arteries With Ventricular Septal Defect and Pulmonary Outflow Tract Obstruction: A 10-Year Follow-Up," Ann Thorac Surg, 2003, 76:1383-8 (Pages).

(Continued)

*Primary Examiner* — Brian Szmal
(74) *Attorney, Agent, or Firm* — Holland & Hart

(57) ABSTRACT

An apparatus comprising a blood vessel measuring device is disclosed. The blood vessel measuring device may comprise a handle. A measuring member may be attached to the handle. The measuring member may be dimensioned to wrap around a blood vessel to measure a size of the blood vessel. The blood vessel measuring device may comprise an extension, and a first end of the extension may be attached to the handle. The blood vessel measuring device may comprise a connector attached to a second end of the extension. A method is also disclosed. The method may comprise inserting a measuring device into an incision in a patient. The measuring device may comprise a measuring member. The method may also comprise wrapping the measuring member around a blood vessel of the patient and measuring a dimension of the blood vessel with the measuring member.

38 Claims, 4 Drawing Sheets

(56) References Cited

U.S. PATENT DOCUMENTS

| | | | |
|---|---|---|---|
| 5,599,173 A | 2/1997 | Chen et al. | |
| 5,755,770 A | 5/1998 | Ravenscroft | |
| 5,776,185 A | 7/1998 | Verona et al. | |
| 5,810,708 A | 9/1998 | Woodard et al. | |
| 5,871,537 A | 2/1999 | Holman et al. | |
| 5,931,842 A | 8/1999 | Goldsteen et al. | |
| 5,941,908 A | 8/1999 | Goldsteen et al. | |
| 5,965,086 A | 10/1999 | Rose et al. | |
| 5,972,017 A | 10/1999 | Berg et al. | |
| 5,976,178 A | 11/1999 | Goldsteen et al. | |
| 6,001,056 A | 12/1999 | Jassawalla et al. | |
| 6,001,124 A | 12/1999 | Bachinski | |
| 6,013,190 A | 1/2000 | Berg et al. | |
| 6,016,810 A | 1/2000 | Ravenscroft | |
| 6,036,702 A | 3/2000 | Bachinski et al. | |
| 6,048,362 A | 4/2000 | Berg | |
| 6,059,823 A | 5/2000 | Holman et al. | |
| 6,068,654 A | 5/2000 | Berg et al. | |
| 6,074,416 A | 6/2000 | Berg et al. | |
| 6,113,612 A | 9/2000 | Swanson et al. | |
| 6,120,432 A | 9/2000 | Sullivan et al. | |
| 6,136,007 A | 10/2000 | Goldsteen et al. | |
| 6,146,325 A | 11/2000 | Lewis et al. | |
| 6,152,937 A | 11/2000 | Peterson et al. | |
| 6,152,945 A | 11/2000 | Bachinski et al. | |
| 6,152,956 A | 11/2000 | Pierce | |
| 6,186,942 B1 | 2/2001 | Sullivan et al. | |
| 6,186,986 B1 | 2/2001 | Berg et al. | |
| 6,200,260 B1 | 3/2001 | Bolling | |
| 6,206,912 B1 | 3/2001 | Goldsteen et al. | |
| 6,235,054 B1 | 5/2001 | Berg et al. | |
| 6,261,315 B1 | 7/2001 | St. Germain et al. | |
| 6,273,880 B1 | 8/2001 | Bert et al. | |
| 6,293,965 B1 | 9/2001 | Berg et al. | |
| 6,299,575 B1 | 10/2001 | Bolling | |
| 6,302,905 B1 | 10/2001 | Goldsteen et al. | |
| 6,309,416 B1 | 10/2001 | Swanson et al. | |
| 6,319,276 B1 | 11/2001 | Holman et al. | |
| 6,346,071 B1 | 2/2002 | Mussivand | |
| 6,352,554 B2 | 3/2002 | De Paulis | |
| 6,371,982 B2 | 4/2002 | Berg et al. | |
| 6,387,037 B1 | 5/2002 | Bolling et al. | |
| 6,390,969 B1 | 5/2002 | Bolling et al. | |
| 6,416,527 B1 | 7/2002 | Berg et al. | |
| 6,428,464 B1 | 8/2002 | Bolling | |
| 6,432,131 B1 | 8/2002 | Ravenscroft | |
| 6,440,163 B1 | 8/2002 | Swanson et al. | |
| 6,443,884 B1 | 9/2002 | Miyawaki | |
| 6,450,171 B1 | 9/2002 | Buckberg et al. | |
| 6,451,033 B1 | 9/2002 | Berg et al. | |
| 6,451,048 B1 | 9/2002 | Berg et al. | |
| 6,475,222 B1 | 11/2002 | Berg et al. | |
| 6,508,252 B1 | 1/2003 | Berg et al. | |
| 6,508,822 B1 | 1/2003 | Peterson et al. | |
| 6,511,491 B2 | 1/2003 | Grudem et al. | |
| 6,514,196 B1 | 2/2003 | Sullivan et al. | |
| 6,533,812 B2 | 3/2003 | Swanson et al. | |
| 6,575,921 B2 * | 6/2003 | Vanden Hoek et al. | 600/587 |
| 6,599,303 B1 | 7/2003 | Peterson et al. | |
| 6,610,004 B2 | 8/2003 | Viole et al. | |
| 6,613,002 B1 * | 9/2003 | Clark et al. | 600/593 |
| 6,620,176 B1 | 9/2003 | Peterson et al. | |
| 6,666,832 B1 | 12/2003 | Carranza et al. | |
| 6,669,720 B1 | 12/2003 | Pierce | |
| 6,673,084 B1 | 1/2004 | Peterson et al. | |
| 6,692,523 B2 | 2/2004 | Holman et al. | |
| 6,702,829 B2 | 3/2004 | Bachinski et al. | |
| 6,726,648 B2 | 4/2004 | Kaplon et al. | |
| 6,746,463 B1 | 6/2004 | Schwartz | |
| 6,749,598 B1 | 6/2004 | Keren et al. | |
| 6,773,453 B2 | 8/2004 | Ravenscroft | |
| 6,802,806 B2 | 10/2004 | McCarthy et al. | |
| 6,805,692 B2 | 10/2004 | Muni et al. | |
| 6,863,677 B2 | 3/2005 | Breznock | |
| 6,889,082 B2 | 5/2005 | Bolling et al. | |
| 6,920,882 B2 | 7/2005 | Berg et al. | |
| 6,926,689 B2 | 8/2005 | Scheule | |
| 6,960,219 B2 | 11/2005 | Grudem et al. | |
| 6,994,666 B2 | 2/2006 | Shannon et al. | |
| 7,014,618 B2 * | 3/2006 | Carranza et al. | 600/587 |
| 7,025,773 B2 | 4/2006 | Gittings et al. | |
| 7,029,483 B2 | 4/2006 | Schwartz | |
| 7,048,681 B2 | 5/2006 | Tsubouchi et al. | |
| 7,077,801 B2 | 7/2006 | Haverich | |
| 7,094,248 B2 | 8/2006 | Bachinski et al. | |
| 2001/0004675 A1 | 6/2001 | Woodard et al. | |
| 2001/0027287 A1 | 10/2001 | Scmulewitz et al. | |
| 2001/0049553 A1 | 12/2001 | De Paulis | |
| 2002/0040235 A1 | 4/2002 | Holman et al. | |
| 2002/0045846 A1 | 4/2002 | Kaplon et al. | |
| 2002/0128703 A1 | 9/2002 | Ravenscroft | |
| 2002/0198603 A1 | 12/2002 | Buckberg et al. | |
| 2003/0040765 A1 | 2/2003 | Breznock | |
| 2003/0083738 A1 | 5/2003 | Holman et al. | |
| 2003/0176830 A1 | 9/2003 | Scheule | |
| 2003/0208257 A1 | 11/2003 | Holman et al. | |
| 2003/0220684 A1 | 11/2003 | Holman et al. | |
| 2004/0059178 A1 | 3/2004 | McCarthy et al. | |
| 2004/0082910 A1 | 4/2004 | Constantz et al. | |
| 2004/0097900 A1 | 5/2004 | Keren et al. | |
| 2004/0162608 A1 | 8/2004 | Haverich | |
| 2004/0181126 A1 | 9/2004 | Buckberg et al. | |
| 2004/0193004 A1 | 9/2004 | Tsubouchi et al. | |
| 2004/0199191 A1 | 10/2004 | Schwartz | |
| 2004/0210202 A1 | 10/2004 | Weinstein | |
| 2004/0215321 A1 | 10/2004 | Holman et al. | |
| 2005/0119688 A1 | 6/2005 | Bergheim | |
| 2005/0149093 A1 | 7/2005 | Pokorney | |
| 2005/0154411 A1 | 7/2005 | Breznock et al. | |
| 2005/0197527 A1 * | 9/2005 | Bolling | 600/37 |
| 2005/0209502 A1 | 9/2005 | Schmid et al. | |
| 2005/0251187 A1 | 11/2005 | Beane et al. | |
| 2005/0256363 A1 | 11/2005 | Bolling et al. | |
| 2005/0261759 A1 | 11/2005 | Lambrecht et al. | |
| 2006/0014999 A1 | 1/2006 | Heilman et al. | |
| 2006/0030747 A1 | 2/2006 | Kantrowitz et al. | |
| 2006/0036313 A1 | 2/2006 | Vassiliades | |
| 2006/0074271 A1 | 4/2006 | Cotter | |
| 2006/0079736 A1 | 4/2006 | Chin et al. | |
| 2006/0089707 A1 | 4/2006 | Vassiliades et al. | |
| 2006/0161133 A1 | 7/2006 | Laird et al. | |
| 2006/0161193 A1 | 7/2006 | Beane et al. | |
| 2008/0215134 A1 | 9/2008 | Lawrence-Brown | |
| 2010/0160847 A1 | 6/2010 | Braido et al. | |
| 2010/0160939 A1 | 6/2010 | Braido | |
| 2010/0161040 A1 | 6/2010 | Braido et al. | |

OTHER PUBLICATIONS

Behrendt, D., et al., "Relief of left ventricular outflow tract obstruction in infants and small children with valved extra cardiac conduits," Ann Thorac Surg., 1987; 43(1):82-6 ( Pages).

Bickers, G., et al., "Gastroesophageal deformities of left ventricular-abdominal aortic conduit," AJR Am J Roentgenol, May 1982; 138(5):867-9 (Pages).

Marino, S. Bradley, et al., "Early Results of the Ross Procedure in Simple and Complex Left Heart Disease," Circulation, 1999; 10:II-162-6 (Pages).

Brown, J., et al., "Long-Term Results of Apical Aortic Conduits in Children With Complex Left Ventricular Outflow Tract Obstruction," Ann Thorac Surg., 2005; 80:2301-8 (Pages).

Ugorji, C., et al., "Post-Traumatic Apical Left Ventricular Aneurysm in a Patient with Left Ventricular Apical-Abdominal Aortic Conduit: Case Presentation," Cardiovascular Diseases, Bulletin of the Texas Heart Institute, 1979; 6:4 (Pages).

Crestanello, J., et al., "Is there a role for the left ventricle apical-aortic conduit for acquired aortic stenosis?", J Heart Valve Dis. Jan. 2004; 13(1):57-62; discussion 62-3 (Pages).

Cooley, Denton, A., et al., "Left Ventricle to Abdominal Aorta Conduit for Relief of Aortic Stenosis," Cardiovascular Diseases, Bulleting of the Texas Heart Institute, 1975, 2; 3 (Pages).

Fogel, M., et al, "Evaluation and follow-up of patients with left ventricular apical to aortic conduits with 2D and 3D magnetic reso-

(56) References Cited

OTHER PUBLICATIONS nance imaging and Doppler echocardiography: A new look at an old operation," American Heart Journal, 2001; 141:630-6 (Pages).

Frommelt, P., et al., "Natural history of apical left ventricular to aortic conduits in pediatric patients," Circulation, Nov. 1991; 84(5Suppl):III213-8 (Pages).

Gammie, J., et al., "Aortic valve bypass for the high-risk patient with aortic stenosis," Annals of Thoracic Surgery, 2006; 81:1605-1611 (Pages).

Koul, B., et al., "Aortoventriculoplasty *ad modum* Konno. Experience with five cases," Scand J. Thorac Cardiovasc Surg., 1984; 18(3):239-42 (Pages).

Misbach, G., et al., "Left ventricular outflow enlargement by the Konno procedure," Journal of Thoracic Cardiovascular Surgery, Nov. 1982; 84(5):696-703 (Pages).

Miyawaki, F., et al., "Recovery directed left ventricular assist device; a new concept," ASAIO J, May-Jun. 2000; 46(3)361-6 (Pages).

Norwood Wi, et al., "Management of infants with left ventricular outflow obstruction by conduit interposition between the ventricular apex and thoracic aorta," J Thorac Cardiovasc Surg., Nov. 1983; 86(5):771-6 (Pages).

Rocchini, A., et al., "Clinical and hemodynamic follow-up of left ventricular to aortic conduits in patients with aortic stenosis," J Am Coll Cardiol., Apr. 1983; 1(4):1135-43 (Pages).

Serraf, A., et al., "Surgical Treatment of Subaortic Stenosis: A Seventeen-Year Experience," J Thorac Cardiovasc Surg., 1999; 117:669-78 (Pages).

Vassiliades, T., "Off-pump apicoaortic conduit insertion for high-risk patients with aortic stenosis," European Journal of Cardio-thoracic Surgery, 2003; 23:156-8 (Pages).

Vigano, M., et al., "Modified method for Novacor left ventricular assist device implantation," Ann Thorac Surg., Jan. 1996; 61(1):247-9 (Pages).

PCT International Search Report for International Application No. PCT/US2009/006582, mailed Mar. 29, 2010 (5 pp.).

\* cited by examiner

APPARATUS AND METHOD FOR MEASURING BLOOD VESSELS

BACKGROUND

Aortic valve replacement is a cardiac surgery procedure that replaces a patient's aortic valve with a prosthetic valve. Aortic valve replacement typically requires open heart surgery, which may be risky and/or impractical for many patients. Aortic valve replacement may not be an option for patients with aortic stenosis, left ventricular outflow obstruction, a heavily calcified ascending aorta, a heavily calcified aortic root, and/or other high risk medical conditions. For example, patients with conditions that preclude a median sternotomy may not be candidates for an aortic valve replacement operation.

Apical aortic conduits may provide a less invasive alternative to aortic valve replacement. An apical aortic conduit may be connected between the apex of the heart and the aorta in a procedure similar to a coronary artery bypass graft. Apical aortic conduits may improve blood flow between the heart and the aorta by bypassing a diseased or malfunctioning aortic valve. Patients who are not eligible for aortic valve replacement may be treated by using an apical aortic conduit to bypass the valve. For example, apical aortic conduits may be used in pediatric patients. The native valve may be left in place in pediatric patients to eliminate the need for periodic valve replacements as the patient grows. Thus, the apical aortic conduit may maintain the maximum possible function of the native valve while bypassing the restricted flow to lessen stress on the heart and allow more blood flow to the body. In other words, the apical aortic conduit may bypass the native valve to allow for extra flow to the aorta while still allowing the maximum flow that the native valve can physiologically handle.

Traditional apical aortic conduits may fail or malfunction for various reasons. For example, the conduit material used in an apical aortic conduit may become blocked as a result of kinking. Traditional conduits may also become occluded and obstruct apical flow. Also, apical aortic conduits are typically sutured to the heart and the aorta, and the suturing may cause aneurisms at or near the attachment site. Apical aortic conduits may also cause gastrointestinal complications such as dysphagia and gastric erosion.

SUMMARY

In various embodiments, an apparatus may comprise a blood vessel measuring device. The blood vessel measuring device may comprise a handle and a measuring member attached to the handle, and the measuring member may be dimensioned to wrap around a blood vessel to measure the size of the blood vessel. According to some embodiments, the blood vessel measuring device may comprise an extension with first and second ends. The first end may be attached to the handle and the second end may be attached to the measuring member.

According to at least one embodiment, the extension may comprise a shape memory material. In some embodiments, the measuring member may comprise a measuring tape. The measuring tape may comprise a shape memory material. According to various embodiments, the measuring member may comprise at least one of a self-expanding or a self-collapsing material.

According to certain embodiments, the blood vessel measuring device may comprise an extension and a connector. The connector may attach a first end of the measuring member to the extension, and the connector may comprise an opening dimensioned to receive a second end of the measuring member. In some embodiments, the measuring member may comprise a cylinder of shape memory material. According to at least one embodiment, the measuring member may comprise at least one of a circular shape or an elliptical shape.

In various embodiments, a method may comprise inserting a measuring device into an incision in a patient. The measuring device may comprise a measuring member. The method may also comprise wrapping the measuring member around a blood vessel of the patient and measuring a dimension of the blood vessel with the measuring member. According to at least one embodiment, the method may comprise placing the measuring member near the blood vessel in an expanded position. The method may further comprise releasing the measuring member to allow the measuring member to collapse to a closed position around the blood vessel.

In some embodiments, the dimension may be a circumference of the blood vessel. According to at least one embodiment, the dimension may be a width of a region available for attaching a connector to the blood vessel. In various embodiments, the measuring member may be attached to a handle. According to certain embodiments, a connector may attach a first end of the measuring member to an extension, and the connector may comprise an opening dimensioned to receive a second end of the measuring member.

In various embodiments, a blood vessel measuring device may comprise a handle and an extension. A first end of the extension may be attached to the handle, and a connector may be attached to a second end of the extension. A measuring member may be attached to the connector, and the measuring member may be dimensioned to wrap around a blood vessel to measure the size of the blood vessel.

According to various embodiments, the connector may comprise an opening dimensioned to receive a second end of the measuring member. In at least one embodiment, the measuring member may comprise circumferential measuring marks for measuring a circumference of the blood vessel. According to some embodiments, the measuring member may comprise width measuring marks for measuring a width of a region available for attaching a connector to the blood vessel. In some embodiments, the extension may comprise a shape memory material and the measuring member may comprise a measuring tape.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are part of the specification. Together with the following description these drawings demonstrate and explain various principles of the instant disclosure.

Figure 1:
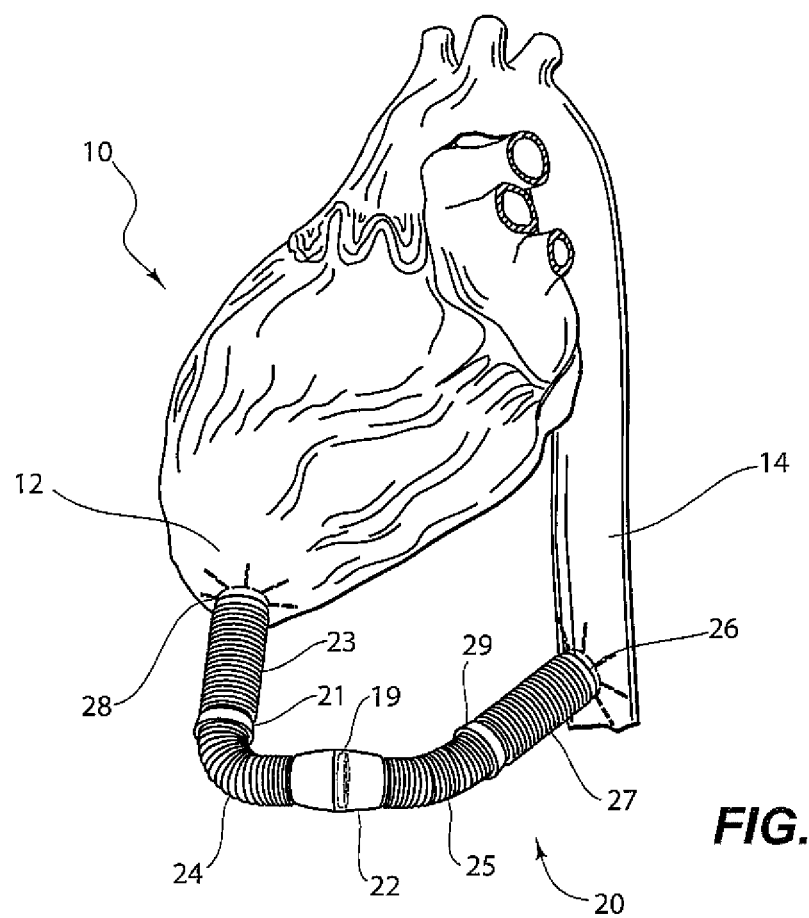
FIG. 1 is a perspective view of an exemplary cardiovascular conduit system attached to a heart according to certain embodiments.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Throughout the drawings, identical reference characters and descriptions indicate similar, but not necessarily identical, elements. While embodiments of the instant disclosure are susceptible to various modifications and alternative forms, specific embodiments have been shown by way of example in the drawings and will be described in detail herein. However, one of skill in the art will understand that embodiments of the instant disclosure are not intended to be limited to the particular forms disclosed herein. Rather, the instant disclosure covers all modifications, equivalents, and alternatives falling within the scope of embodiments defined by the appended claims.

A physician may implant a cardiovascular conduit system to circumvent a restriction in blood flow. For example, a physician may use a cardiovascular conduit system to bypass an aortic valve in a patient with aortic valve stenosis. Similarly, a cardiovascular conduit system may be used to bypass a pulmonary valve in a patient with pulmonary valve stenosis. Physicians may also use cardiovascular conduit systems to address various other problems and diseases in a patient's cardiovascular system.

Cardiovascular conduit systems may provide various advantages over prior systems. Physicians may implant a cardiovascular conduit system on a beating heart. Procedures performed on a beating heart may be referred to as off-pump procedures, and off-pump procedures may be less invasive than on-pump procedures (i.e., procedures that require cardiopulmonary bypass). In some embodiments, cardiovascular conduit systems may be used with traditional surgical techniques (e.g., on-pump procedures). In traditional surgical techniques, cardiovascular conduit systems may provide various advantages, such as reduced pump time and smaller incisions. Connectors in a cardiovascular conduit system may be designed to reduce the risk of aneurisms at the attachment site. The conduit in a cardiovascular conduit system may be kink and occlusion resistant. Cardiovascular conduit systems may also reduce the risk of gastrointestinal complications. The following disclosure presents numerous other features and advantages of cardiovascular conduit systems.

FIG. 1 shows a cardiovascular conduit system 20 connecting a left ventricle 12 of a heart 10 to an aorta 14. Conduit system 20 may include a connector 28 attached to an apex of heart 10. Connector 28 may also be attached to a first end of a conduit section 23. Various examples of cardiovascular conduits and connectors are shown and discussed in U.S. patent application Ser. No. 12/340,280, filed on 19 Dec. 2008, and entitled "Systems, Apparatuses, and Methods for Cardiovascular Conduits and Connectors," the disclosure of which is incorporated in its entirety in this reference.

A second end of conduit section 23 may be attached to a connector 21, and connector 21 may be attached to a first end of a conduit section 24. A second end of conduit section 24 may be attached to a valve housing 22 that includes a valve 19. Valve 19 may control the flow of blood between left ventricle 12 and aorta 14. Various examples of valves and valve housings are illustrated and described in U.S. patent application Ser. No. 12/340,189, filed on 19 Dec. 2008, and entitled "Cardiovascular Valve and Valve Housing Apparatuses and Systems," the disclosure of which is incorporated in its entirety by this reference.

Valve housing 22 may also be connected to a first end of a conduit section 25, and a second end of conduit section 25 may be attached to a connector 29. A first end of a conduit section 27 may be attached to connector 29, and a second end of conduit section 27 may be attached to a connector 26. Connector 26 may attach conduit section 27 to aorta 14. The conduit system shown in FIG. 1 may be referred to as an apical aortic conduit system because it connects an apex of heart 10 (at left ventricle 12) to aorta 14.

According to various embodiments, several sizes of cardiovascular-conduit-system connectors may be available to a physician. In order to select the best aortic connector for use with a particular patient, a physician may determine the size of the patient's aorta. Typical aortas may range from 20-50 millimeters (mm) in diameter, and some patients' aortas may be smaller than 20 mm or larger than 50 mm. An aortic connector that is too large for a patient's aorta may not fit into the aorta properly. On the other hand, an aortic connector that is too small may not provide optimal blood flow. The blood vessel measuring devices and methods disclosed herein may allow a physician to determine the size of a patient's aorta and avoid the problems associated with improperly sized connectors.

A physician may measure the size of a patient's aorta (or other blood vessel) to determine the appropriately sized connector, conduit, valve, cutting device (e.g., coring device), tube, and/or other tools for implanting a cardiovascular conduit system. Various examples of cutting devices and valves are illustrated and described in U.S. patent application Ser. No. 12/340,431, filed on Dec. 19, 2008, and entitled "Systems, Apparatuses, and Methods for Cardiovascular Cutting Devices and Valves," the disclosure of which is incorporated in its entirety by this reference.

Blood vessels may be any veins or arteries in a cardiovascular system. Blood vessel measuring devices disclosed herein may be designed to measure large blood vessels such as the aorta and/or the pulmonary artery. Blood vessel measuring devices may also be designed to measure various other blood vessels.

Figure 2:
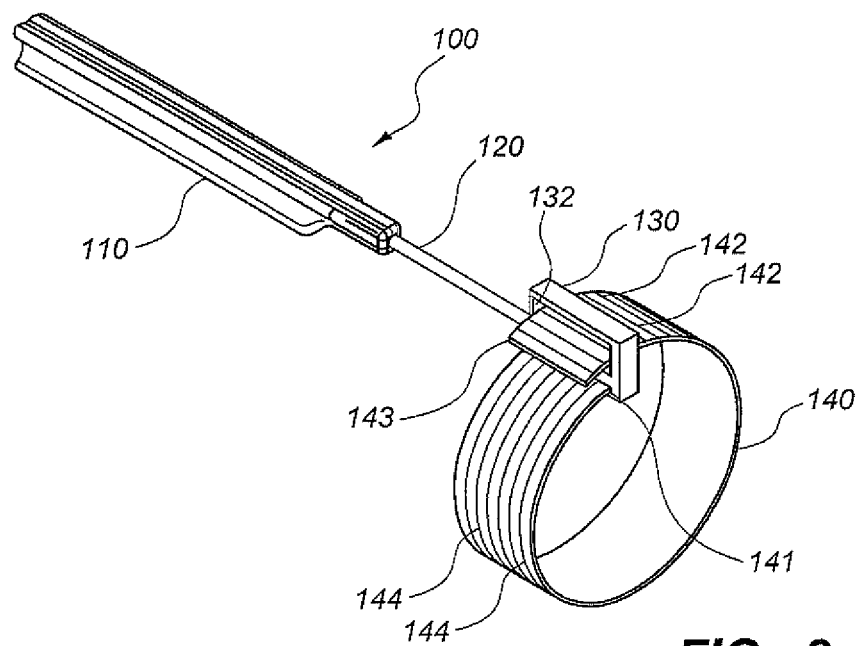
FIG. 2 is a perspective view of an exemplary blood vessel measuring device according to certain embodiments.

FIG. 2 illustrates a blood vessel measuring device 100. Blood vessel measuring device 100 may include a handle 110, an extension 120, a connector 130, and a circular measuring member 140. Measuring member 140 may include measuring marks 142, which may be in increments of centimeters, inches, or any other suitable measurement unit. A physician may use measuring marks 142 to determine the circumference of a patient's blood vessel. Thus, measuring marks 142 may be referred to as circumferential measuring marks. A physician may determine the circumference of a patient's blood vessel by positioning measuring member 140 around a patient's aorta and reading measuring marks 142, as will be discussed in the disclosure corresponding to FIGS. 3-6.

Handle 110 may be attached to extension 120, and extension 120 may be attached to connector 130, as shown in FIG. 2. In other embodiments, handle 110 may be directly attached to connector 130 or measuring member 140. Handle 110 may be any suitable shape and/or size. According to some embodiments, handle 110 may be ergonomically shaped for optimal surgeon control and comfort. Handle 110 may be made of any suitable material. In some embodiments, handle 110 may be brightly colored to help the physician see and guide blood vessel measuring device 100 during a procedure. Handle 110 may be textured to provide slip resistance. In some embodiments, handle 110 may be made of a shape memory material that allows handle 110 to be flexible, which may help a physician properly position blood vessel measuring device 100 for measuring a patient's aorta or other blood vessel.

As previously noted, extension 120 may attach handle 110 to connector 130. Extension 120 may be a rod, bar, or shaft of any suitable shape and/or size. Extension 120 may be made of a shape memory material or any other suitable material. Shape memory materials may include shape memory alloys, which may also be referred to as smart alloys or memory metals. A shape memory material may be a copper-zinc-aluminum alloy, a copper-aluminum-nickel alloy, a nickel-titanium alloy (e.g., NITINOL), or any other suitable shape memory alloy. The flexibility of extension 120 may help a physician properly position blood vessel measuring device 100 for measuring a blood vessel.

Figure 4:
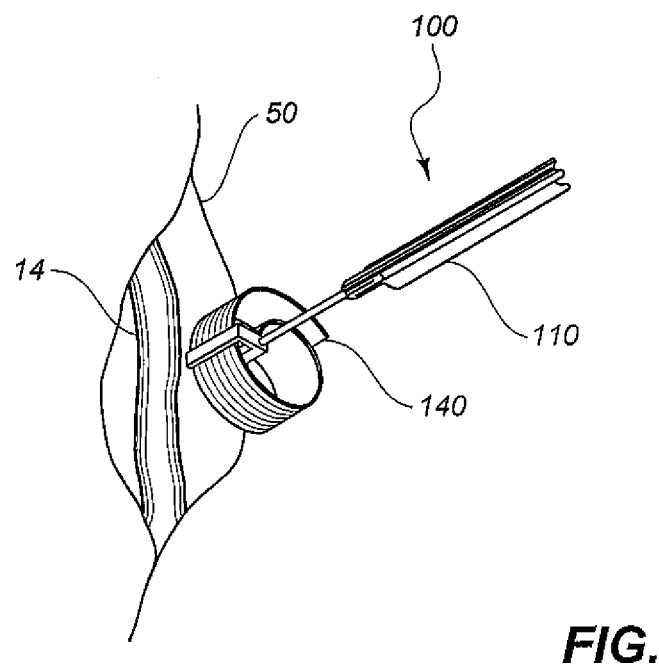
FIG. 4 is a perspective view of a blood vessel measuring device being inserted into an incision according to certain embodiments.
Figure 5:
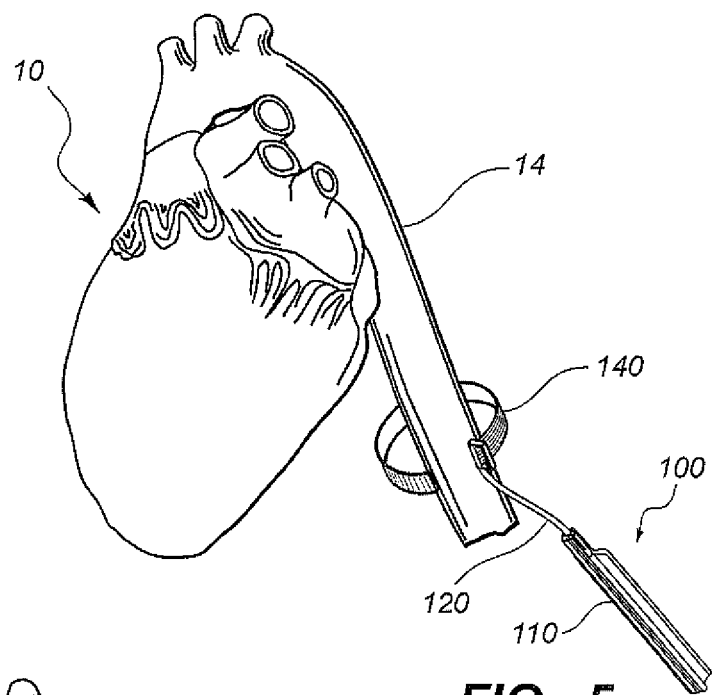
FIG. 5 is a perspective view of a measuring member of the blood vessel measuring device being placed around an aorta according to certain embodiments.
Figure 6:
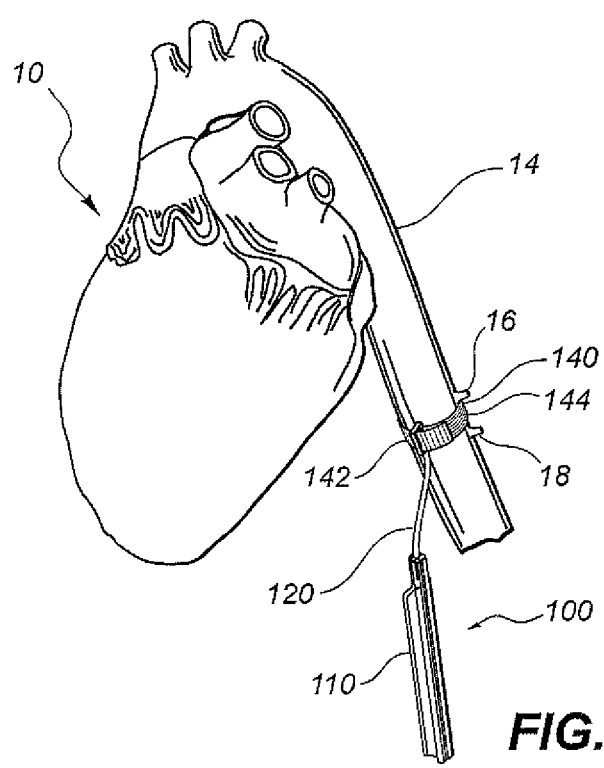
FIG. 6 is a perspective view showing measuring of an aorta with the blood vessel measuring device shown in FIG. 5.

FIG. 2 shows that connector 130 may attach extension 120 to an end 141 of measuring member 140. An end 143 of measuring member 140 may extend through an opening 132 in connector 110. Opening 132 may help a physician determine the circumference of a blood vessel. For example, a physician may determine a circumference of the blood vessel by reading the measuring mark on end 143 that is closest to opening 132. The measuring member 140 may be oriented perpendicular to a longitudinal dimension of the extension 120 and the handle 110 as shown in FIGS. 2-6. When the measuring member 140 wraps around a blood vessel as shown in FIGS. 5 and 6, the extension 120 and handle 110 are generally aligned parallel with a longitudinal dimension of the blood vessel.

Measuring member 140 may be a measuring tape or any other suitable measuring device. Measuring member 140 may be semi-rigid and may be made of any suitable material, including plastic or metal. Measuring member 140 may also be made of a shape memory material. In some embodiments, measuring member 140 may be reinforced with plastic or metal inserts to provide additional rigidity. The rigidity of measuring member 140 may help measuring member 140 return from an open position (i.e., a position where end 143 is pulled out of opening 132 and away from connector 130) to a closed position (i.e., a position where end 143 passes through opening 132).

As previously noted, measuring member 140 may include marks 142 for taking circumferential measurements. Marks 142 may allow a physician to measure the circumference of a blood vessel and determine a diameter of the blood vessel. Measuring member 140 may also include marks 144 for taking width measurements. In some embodiments, marks 144 may be horizontal to marks 142. Marks 144 may be in increments of centimeters, inches, or any other suitable measurement unit. Marks 144 may help a physician determine how much space is available (e.g., a width of a region available) for attaching a connector to the blood vessel.

Marks 142 and 144 may be any type of suitable measuring indication. In some embodiments, marks 142 and/or 144 may be lines with corresponding measurement numbers. According to various embodiments, marks 142 and/or 144 may be indents or bumps. In such embodiments, a physician may be able to determine an aorta's size by feeling, rather than reading, marks 142 and/or 144.

Measuring member 140 may be designed to measure a blood vessel as the diameter of the blood vessel changes due to systolic and diastolic pressures. The diameter of a blood vessel may change ten to fifteen percent under systolic and diastolic pressures. The diameter of a blood vessel may also change less than ten or more than fifteen percent under systolic and diastolic pressures, and measuring member 140 may be designed to accommodate these diameter fluctuations.

Measuring member 140 may be made of a resilient material that maintains constant pressure on the blood vessel as the diameter of the blood vessel changes. For example, measuring member 140 may be made of a shape memory material that applies slight pressure to the blood vessel and changes diameter as the blood vessel changes diameter. A physician may be able to determine both the larger and smaller diameters of the blood vessel, which may enable the physician to choose the most appropriate connector for the blood vessel. In some embodiments, handle 110 may have a gauge (or any other suitable measurement indicator) that displays the diameter and/or circumference of measuring member 140. Thus, a physician may be able to read the gauge to determine the size of the blood vessel as it changes.

Figure 3:
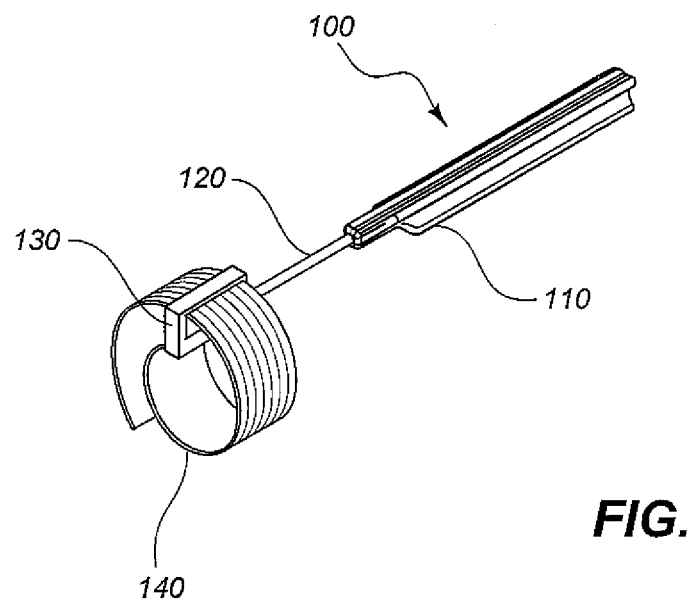
FIG. 3 is a perspective view of the blood vessel measuring device illustrated in FIG. 2.

FIG. 3 shows that measuring member 140 may collapse (e.g., wind-up) to allow it to have a smaller diameter. Measuring member 140 may be self-collapsing (e.g., resilient enough to collapse to a certain diameter without the aid of a physician) to a predetermined diameter. Measuring member 140 may also be self-expanding. The collapsibility of measuring member 140 may allow measuring member 140 to be inserted into a smaller incision. In some embodiments, a physician may hold measuring member 140 in a collapsed position while inserting measuring member 140 into an incision in a user. In other embodiments, blood vessel measuring device 100 may include a retaining member that holds measuring member 140 in a collapsed position for insertion into an incision. A physician may release the retaining member to allow measuring member 140 to expand after measuring member 140 is inserted through the incision. FIG. 4 illustrates blood vessel measuring device 100 being inserted into an incision 50 in a patient. As shown in FIG. 4, blood vessel measuring device 100 may be inserted toward aorta 14.

FIGS. 5 and 6 show blood vessel measuring device 100 with measuring member 140 placed around aorta 14. A physician may wrap measuring member 140 around aorta 14. In some embodiments, measuring member 140 may be made of a shape memory material (or any other suitable resilient material) that springs into a closed position from an open position. Thus, a physician may place measuring member 140 partially around aorta 14, as shown in FIG. 5, and then release measuring member 140. After being released, measuring member 140 may spring to a closed measuring position (as shown in FIG. 6) without additional help from the physician.

The physician may tighten measuring member 140 until it is snug around aorta 14 and capable of measuring the diameter of aorta 14. In various embodiments, measuring member 140 may be resilient enough that it tightens around aorta 14 without additional tightening by the physician. After measuring member 140 is tightened around aorta 14, the physician may look at marks 142 to determine the size of aorta 14. In other embodiments, the physician may use a biomedical optical device to view marks 142 on measuring member 140. According to at least one embodiment, blood vessel measuring device 100 may include an electronic measurement system in addition to or instead of marks 142 and 144. For example, blood vessel measuring device 100 may include a button on handle 110. When a physician presses the button, blood vessel measuring device 100 may take a measurement of the circumference and/or diameter of measuring member 140.

FIG. 6 shows that measuring member 140 may be positioned between arteries 16 and 18. Measuring marks 144 may allow a physician to determine how much space between arteries 16 and 18 is available for inserting a connector (i.e., a physician may read measuring marks 144 to determine a distance between arteries 16 and 18). A physician may choose a connector with a diameter equal to or smaller than the distance between arteries 16 and 18 if the physician desires to place the connector between arteries 16 and 18.

FIGS. 5 and 6 show that extension 120 may be bendable. A bendable extension, such as extension 120, may help a physician navigate around other organs in the patient to properly position measuring member 140 around the aorta. In some embodiments, extension 120 may be detachable from both handle 110 and connector 130. Extension 120 may be interchangeable with extensions of other shapes and sizes. For example, a physician may use a longer extension for larger patients and a shorter extension for smaller patients.

Figure 7:
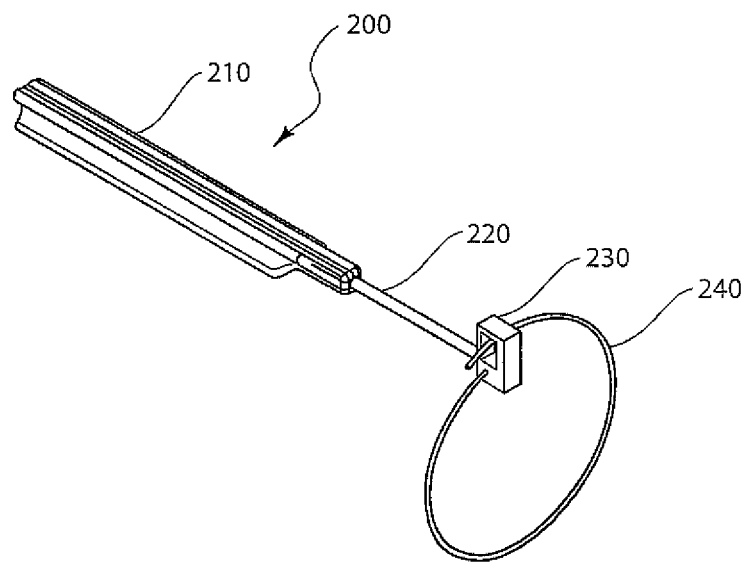
FIG. 7 is a perspective view of an exemplary blood vessel measuring device according to certain embodiments.

FIG. 7 illustrates a blood vessel measuring device 200. As shown in FIG. 7, blood vessel measuring device 200 may include a handle 210, an extension 220, a connector 230, and a measuring member 240. Measuring member 240 may be a rod instead of having a cylindrical shape like measuring member 140 shown in FIG. 2. As shown in both FIGS. 2 and 7, measuring members may be circular in shape, mirroring the shape of a blood vessel. According to various embodiments, aorta measuring members may have other shapes or may be designed to conform to other shapes (e.g., elliptical shapes) for use with abnormally-shaped blood vessels.

According to various embodiments, connector 230 and/or measuring member 240 may be transparent or semi-transparent, which may provide a contrast with the indicator marks that allows the physician to more easily read the marks. A transparent or semi-transparent measuring member may also allow the physician to see a surface of the vessel being measured.

Figure 8:
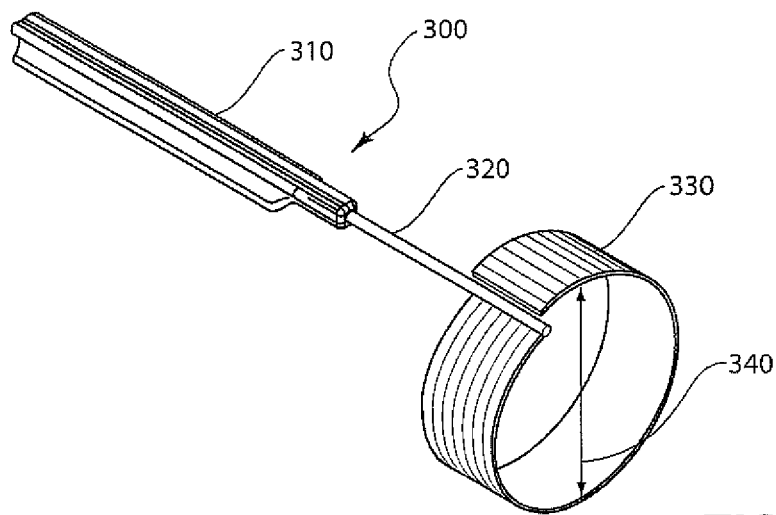
FIG. 8 is a perspective view of an exemplary blood vessel measuring device according to certain embodiments.

FIG. 8 illustrates a blood vessel measuring device 300 with a handle 310, an extension 320, and a measuring member 330. As shown in FIG. 8, a blood vessel measuring device does not necessarily need to include a connector. In at least one embodiment, extension 320 may be directly connected to measuring member 330. In some embodiments, a blood vessel measuring device may not include a separate handle and extension (e.g., extension 320 may be used as a handle). According to at least one embodiment, blood vessel measuring device 300 may not include extension 320, and handle 310 may be directly attached to measuring member 330.

Measuring member 330 may be cylindrical, annular, ring-shaped, curved, rounded, and/or circular. Measuring member 330 may expand and collapse to have a diameter 340 that ranges between 15 mm and 55 mm. In some embodiments, measuring member 330 may expand or collapse to any suitable diameter, including diameters greater than 55 mm or less than 15 mm.

As previously noted, blood vessel measuring devices may help physicians determine the appropriate size of connectors for their patients. Selecting an appropriately-sized connector may reduce the risk of an aneurism at the connection site of the blood vessel and the connector. A properly-sized connector may also optimize blood flow. Accurately sizing connectors for a blood vessel may reduce leakage around the connector, reduce the possibility of vessel dissection, reduce the risk of connector tear-out, and may improve the speed of the implant procedure.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive and that reference be made to the appended claims and their equivalents for determining the scope of the instant disclosure.

Unless otherwise noted, the terms "a" or "an", as used in the specification and claims, are to be construed as meaning "at least one of." In addition, for ease of use, the words "including" and "having", as used in the specification and claims, are interchangeable with and have the same meaning as the word "comprising."

What is claimed is:

1. A blood vessel measuring device comprising:
    a handle;
    a measuring member attached to the handle, the measuring member having a free end, the measuring member being configured to overlap itself in a circumferential direction such that the free end is automatically movable to wrap around a blood vessel to measure a size of the blood vessel while the handle is arranged parallel with a longitudinal dimension of the blood vessel.

2. The device of claim 1, wherein the blood vessel measuring device comprises:
    an extension with first and second ends, the first end being attached to the handle and the second end being attached to the measuring member.

3. The device of claim 2, wherein the extension comprises a shape memory material.

4. The device of claim 1, wherein the measuring member comprises a measuring tape.

5. The device of claim 4, wherein the measuring tape comprises a shape memory material.

6. The device of claim 1, wherein the measuring member comprises at least one of:
    a self-expanding material;
    a self-collapsing material.

7. The device of claim 1, wherein the blood vessel measuring device comprises:
    an extension;
    a connector attaching a first end of the measuring member to the extension, the connector comprising an opening dimensioned to receive a second end of the measuring member.

8. The device of claim 1, wherein the measuring member comprises a cylinder of shape memory material.

9. The device of claim 1, wherein the measuring member comprises at least one of:
    a circular shape;
    an elliptical shape.

10. A method comprising:
    inserting a measuring device into an incision in a patient, the measuring device comprising an adjustable measuring member and a handle, the measuring device extending in a plane perpendicular to a longitudinal dimension of the handle;

wrapping the measuring member completely around a blood vessel of the patient;
measuring a dimension of the blood vessel with the measuring member.

11. The method of claim 10, further comprising:
placing the measuring member near the blood vessel in an expanded position;
releasing the measuring member to allow the measuring member to collapse to a closed position around the blood vessel.

12. The method of claim 10, wherein the dimension is a circumference of the blood vessel.

13. The method of claim 10, wherein the dimension is a width of a region available for attaching a connector to the blood vessel.

14. The method of claim 10, wherein the measuring member is attached to a handle.

15. The method of claim 10, wherein a connector attaches a first end of the measuring member to an extension, and the connector comprises an opening dimensioned to receive a second end of the measuring member.

16. A blood vessel measuring device comprising:
a handle;
an extension, a first end of the extension being attached to the handle;
a connector attached to a second end of the extension;
a measuring member attached to the connector and oriented in a plane perpendicular to a longitudinal dimension of the extension, the measuring member having a free end, the measuring member being configured to overlap itself in a circumferential direction such that the free end is automatically movable to wrap around a blood vessel to measure a size of the blood vessel.

17. The device of claim 16, wherein the connector comprises an opening dimensioned to receive a second end of the measuring member.

18. The device of claim 16, wherein the measuring member comprises circumferential measuring marks for measuring a circumference of the blood vessel.

19. The device of claim 18, wherein the measuring member comprises width measuring marks for measuring a width of a region of the blood vessel.

20. The device of claim 19, wherein the region is suitable for attachment of a cardiovascular conduit system to the blood vessel.

21. The device of claim 16, wherein the extension comprises a shape memory material and the measuring member comprises a measuring tape.

22. A method comprising:
inserting a measuring device into an incision in a patient, the measuring device comprising a measuring member;
wrapping the measuring member around a blood vessel of the patient;
measuring a dimension of the blood vessel with the measuring member;
placing the measuring member near the blood vessel in an expanded position;
releasing the measuring member to allow the measuring member to collapse to a closed position around the blood vessel.

23. The method of claim 22, wherein the dimension is a circumference of the blood vessel.

24. The method of claim 22, wherein the dimension is a width of a region available for attaching a connector to the blood vessel.

25. The method of claim 22, wherein the measuring member is attached to a handle.

26. The method of claim 22, wherein a connector attaches a first end of the measuring member to an extension, and the connector comprises an opening dimensioned to receive a second end of the measuring member.

27. A method comprising:
inserting a measuring device into an incision in a patient, the measuring device comprising a measuring member;
wrapping the measuring member around a blood vessel of the patient;
measuring a dimension of the blood vessel with the measuring member;
wherein a connector attaches a first end of the measuring member to an extension, and the connector comprises an opening dimensioned to receive a second end of the measuring member.

28. The method of claim 27, wherein the dimension is a circumference of the blood vessel.

29. The method of claim 27, wherein the dimension is a width of a region available for attaching a connector to the blood vessel.

30. The method of claim 27, wherein the measuring member is attached to a handle.

31. A blood vessel measuring device comprising:
a handle;
a measuring member attached to the handle, the measuring member having an adjustable size and being dimensioned to wrap around a blood vessel to measure a size of the blood vessel while the handle is arranged parallel with a longitudinal dimension of the blood vessel;
an extension with first and second ends, the first end being attached to the handle and the second end being attached to the measuring member, and the extension comprises a shape memory material.

32. A blood vessel measuring device comprising:
a handle;
a measuring member attached to the handle, the measuring member having an adjustable size and being dimensioned to wrap around a blood vessel to measure a size of the blood vessel while the handle is arranged parallel with a longitudinal dimension of the blood vessel;
wherein the measuring member comprises a measuring tape having a shape memory material.

33. A blood vessel measuring device comprising:
a handle;
a measuring member attached to the handle, the measuring member having an adjustable size and being dimensioned to wrap around a blood vessel to measure a size of the blood vessel while the handle is arranged parallel with a longitudinal dimension of the blood vessel;
wherein the measuring member comprises at least one of a self-expanding material and a self-collapsing material.

34. A blood vessel measuring device comprising:
a handle;
a measuring member attached to the handle, the measuring member having an adjustable size and being dimensioned to wrap around a blood vessel to measure a size of the blood vessel while the handle is arranged parallel with a longitudinal dimension of the blood vessel;
wherein the measuring member comprises a cylinder of shape memory material.

35. A blood vessel measuring device comprising:
a handle;
an extension, a first end of the extension being attached to the handle;
a connector attached to a second end of the extension;
a measuring member attached to the connector and oriented in a plane perpendicular to a longitudinal dimension of the extension, the measuring member being adjustable and dimensioned to wrap around a blood vessel to measure a size of the blood vessel;

wherein the extension comprises a shape memory material and the measuring member comprises a measuring tape.

36. The device of claim 35 wherein the connector comprises an opening dimensioned to receive a second end of the measuring member.

37. The device of claim 35, wherein the measuring member comprises circumferential measuring marks for measuring a circumference of the blood vessel.

38. The device of claim 35, wherein the measuring member comprises width measuring marks for measuring a width of a region available for attaching the connector to the blood vessel.

* * * * *